(12) United States Patent
Le

(10) Patent No.: US 6,797,261 B1
(45) Date of Patent: Sep. 28, 2004

(54) PLASTICISER NAILS

(76) Inventor: Loc Thi Le, 3855 Pacific Coast Hwy., suite 6B, Torrance, CA (US) 90505

( * ) Notice: Subject to any disclaimer, the term of this patent is extended or adjusted under 35 U.S.C. 154(b) by 62 days.

(21) Appl. No.: 10/128,593

(22) Filed: Apr. 23, 2002

(51) Int. Cl.$^7$ .............................. A61K 7/00; A61K 7/04; A45D 29/00

(52) U.S. Cl. .............................. 424/61; 424/401; 132/73

(58) Field of Search ....................... 424/61, 401; 132/73

(56) References Cited

U.S. PATENT DOCUMENTS 5,908,035 A * 6/1999 Carroll et al. ................. 132/73

* cited by examiner

*Primary Examiner*—Thurman K. Page
*Assistant Examiner*—Sharon Howard
(74) *Attorney, Agent, or Firm*—Michael I. Kroll

(57) ABSTRACT

The present invention 10 discloses a method of applying, drying and bonding fingernail polish 26, and more particularly, to the bonding of protective coatings on a fingernail 16 by means of a prescribed process. The preferred method of the present invention 10 is to provide a simple but unique method of drying and bonding protective nail coatings that fortifies the fingernail. This unique method provides for long-lasting, non-yellowing, natural-looking nails 16 that can be worn with or without nail polish 26. The present invention 10 requires the use of instruments including: a UV lamp, acrylic drill, nail file, coarse and medium sanding paper, gel brush, scissors, flat brush, steel brush, cuticle pusher, orange stick, flat brush handle, and anything that is considered tube, squeeze instruments foil or plastic bag. As part of the method of the present invention 10, an acrylic powder blend is mixed with a UV gel compound to form a gel blend/mix.

8 Claims, 10 Drawing Sheets

FLOW CHART OF THE PRESENT INVENTION NAIL TREATMENT PROCESS.

FLOW CHART OF THE PRESENT INVENTION NAIL TREATMENT PROCESS.

FLOW CHART OF THE PRESENT INVENTION NAIL TREATMENT PROCESS.

PLASTICISER NAILS

BACKGROUND OF THE INVENTION

1. Field of the Invention

The present invention relates generally to a method of applying, drying and bonding fingernail polish, and more particularly to the bonding of protective coatings on a fingernail by means of a prescribed process.

The preferred form of the present invention in to provide a simple but unique method of drying and bonding protective nail coatings that fortifies the fingernail. This unique method provides for a long lasting, non-yellowing, natural looking nails that can be worn with or without nail polish.

The present invention requires the use of instruments including; a UV lamp, acrylic drill, nail file, coarse and medium sanding paper, gel brush, scissors, flat brush, steel brush, cuticle pusher, orange stick, flat brush handle, and anything that is considered tube, squeeze instruments foil or plastic bag. The products consists of pink, clear, and natural acrylic power, UV gel, 70% alcohol, polish remover, cuticle oil, white color polish, sheer pink color polish, and when applicable, nail tips and glue.

The first step is to prepare the fingernail by cleaning the surface from any and all foreign material such as might be left over from the previous nail polish coatings or any dirt or removing any oily film that might interfere with the bonding the base layer of nail polish to the surface of the nail. Once this is done then the steps of present new method can begin.

The present invention method begins with a mixing technique that consists of a power mix incorporated of 1 part of pink powder, 1 part of natural powder, and 3 parts of clear power. A second gel mixture is formulated with 1 ounce of clear UV gel and two teaspoons of power mix. Final preparation of the fingernail requires the entire nail plates to be gently filed.

If a nail tips for extended length is desired, the tips are glued at this time. This is followed by the initial covering stage consisting of a thin coat of gel mix on the entire nail's plate using a pusher or other instrument with a flat surface. This is followed by putting the nails under a UV lamp for two minutes. For the next step, apply one more coat of gel nix on the entire nail covering the first coat. The nails are then place back under the UV lamp for three minutes.

After the three minutes, take the nails out from the UV lamp and wipe with alcohol. Using the drill with the coarse side of the sand paper, the entire nail is filed to a desired thickness. This is followed by the shaping of the nail. In the next step the finger nail is turned over to file the underside of the nail and to smooth the edges. Then, using the drill medium side of the sand paper, file to smooth the entire nail assuring the product is attached tightly around the cuticle, but the gel mix is not on the cuticle. Upon completion of the sanding, the dust is removed assuring everything is clean.

If a French manicure is desired, a coat of white polish is applied to the nail tip at this time. The flat brush is used to correct the line of white polish on the nail tip.

At this time one thin coat of clear gel is applied to the entire nail leaving one millimeter away from the cuticle. The nails are then placed under a UV lamp for two minutes. After the two minutes, the gel brush is used to apply one thin coat of clear gel on the entire nail ensuring to cover every coat on the nail carefully. This is followed by placing the nails under the UV lamp for five minutes.

After the five minutes, the nails are wiped with alcohol, cuticle oil is applied and the hand is washed. If desired, color polish is then applied.

2. Description of the Prior Art

There are numerous fingernail treatment processes, while these processes may be suitable for the purposes for which they were designed, they would not be as suitable for the purposes of the present invention as hereinafter described.

Many problems and difficulties often occur in the application of fingernail treatments. Two of the most prevailing problems, however, are in the drying of the various layers or coatings after one or more coating have been applied to the fingernail. The other problem consists of properly bonding a final finished protective clear coat.

After the application of one or more treatment coats have been applied to a fingernail they are often not completely dry to a point wherein the solvents that help form the nail treatment are not completely released from the treatment before a protective coat is applied. Some methods of applying nail treatment use a heat source along which will dry the nail coating, but if not done properly and timely, it does not cause a good bonding between the nail coatings. The coating looks dry but is sometimes left tacky which allows the coating to open to smudging. Furthermore, if the coating is overly dry it becomes susceptible to chipping and cracking.

SUMMARY OF THE PRESENT INVENTION

The present invention discloses a method of applying, drying and bonding fingernail polish, and more particularly, to the bonding of protective coatings on a fingernail by means of a prescribed process. The preferred method of the present invention is to provide a simple but unique method of drying and bonding protective nail coatings that fortifies the fingernail. This unique method provides for long-lasting, non-yellowing, natural-looking nails 16 that can be worn with or without nail polish. The present invention requires the use of instruments including: a UV lamp, acrylic drill, nail file, coarse and medium sanding paper, gel brush, scissors, flat brush, steel brush, cuticle pusher, orange stick, flat brush handle, and anything that is considered tube, squeeze instruments foil or plastic bag. As part of the method of the present invention, an acrylic powder blend is mixed with a UV gel compound to form a gel blend/mix.

A primary object of the present invention is to provide a nail treatment process that provides long lasting protection of the nail.

An additional object of the present invention is to provide a nail treatment process that provides clear, non-yellowing, natural looking nails.

A further object of the present invention is to provide a nail treatment process that is not harmful to the natural nails.

A yet further object of the present invention is to provide a nail treatment process that can be worn with or without nail polish.

Another object of the present invention is to provide a nail treatment process that prevents smudging or cracking of the coverings.

Still another object of the present invention is to provide a nail treatment process that is low in cost to apply.

Further objects of the present invention will appear as the description proceeds.

To the accomplishments of the above and related objects, this invention may be embodied in the form illustrated in the accompanying drawings, attention being called to the fact, however, that the drawings are illustrative only, and that changes may be made in the specific construction illustrated and described in the appended claims.

BRIEF DESCRIPTION OF THE DRAWINGS

Various other objects, features and attendant advantages of the present invention will become more fully appreciated

LIST OF REFERENCE NUMERALS

Figure 1:
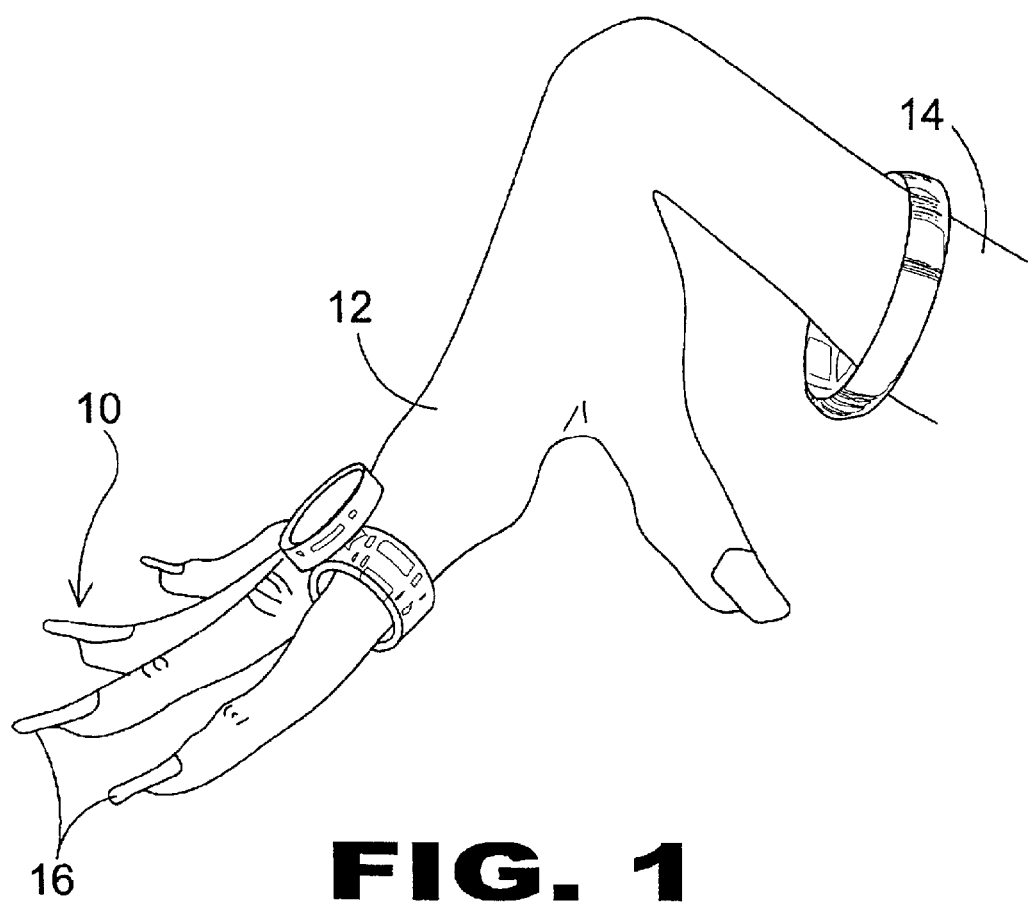
FIG. 1 is an illustrative view of the present invention nail treatment process.

With regard to reference numerals used, the following numbering is used throughout the drawings.

10 present invention
12 hand
14 user
16 fingernails
18 gel blend/mix
20 nail file/drill
22 white polish
24 cuticle
26 nail polish

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative view of the hand 12 of a user 14 with the present invention 10 being a nail treatment process having been applied to the fingernails 16 of the user. The nail treatment process promotes long lasting, clear, non-yellowing, natural looking nails 16. In addition it is not harmful to the natural nails 16 and can be worn with or without nail polish. A UV lamp, acrylic drill, nail file, coarse and medium sanding paper, gel brush, scissors to trim nail tips, flat brush, steel brush, cuticle pusher or other instrument that has a flat surface at the end, orange stick, flat brush handle, anything that is considered a tube, squeeze instruments and a foil or plastic bag are required to attain the nail treatment process.

Figure 2:
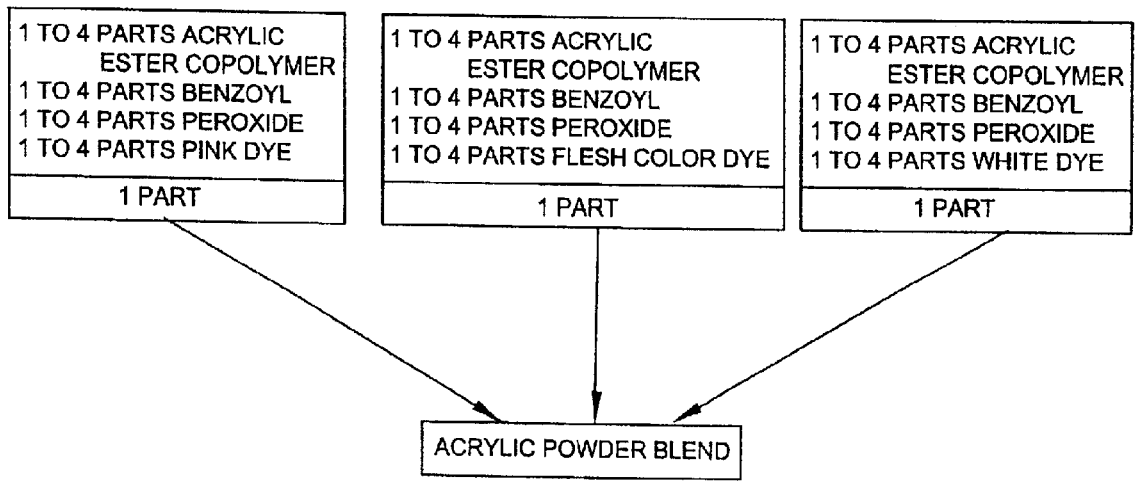
FIG. 2 is an illustrative view of the present invention powder mix components.

Turning to FIG. 2, shown therein is an illustrative view of the steps necessary to prepare or mix the acrylic powder blend of the present invention. The acrylic powder blend is prepared by combining one part pink powder; one part flesh-colored powder; and, one part white powder. The pink powder is made by combining one to four parts acrylic ester copolymer, one to four parts benzoyl, one to four parts peroxide and, one to four parts pink dye. The flesh-colored powder is made by combining one to four parts acrylic ester copolymer, one to four parts benzoyl, one to four parts peroxide, and one to four parts flesh-colored dye. The white powder is made by combining one to four parts acrylic ester copolymer, one to four parts benzoyl, one to four parts peroxide, and one to four parts white dye.

Figure 3:
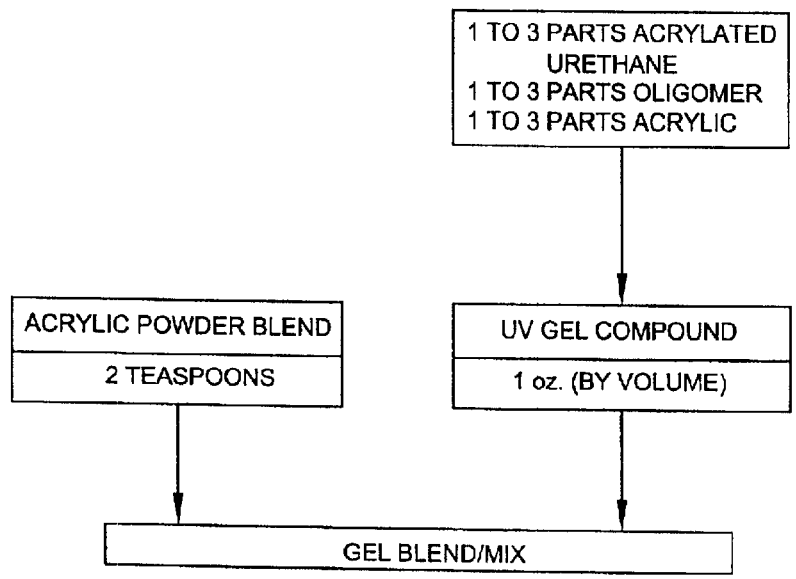
FIG. 3 is an illustrative view of the present invention gel mix components.

Turning to FIG. 3, shown therein is an illustrative view of the steps necessary to prepare or mix the gel blend of the present invention. After the acrylic powder blend is prepared, the gel blend is formulated by mixing two teaspoons of acrylic powder blend with one ounce (by volume) of a UV gel compound. The UV gel compound is prepared by mixing one to three parts acrylated urethane, one to three parts oligomer, and one to there parts acrylic.

Figure 4:
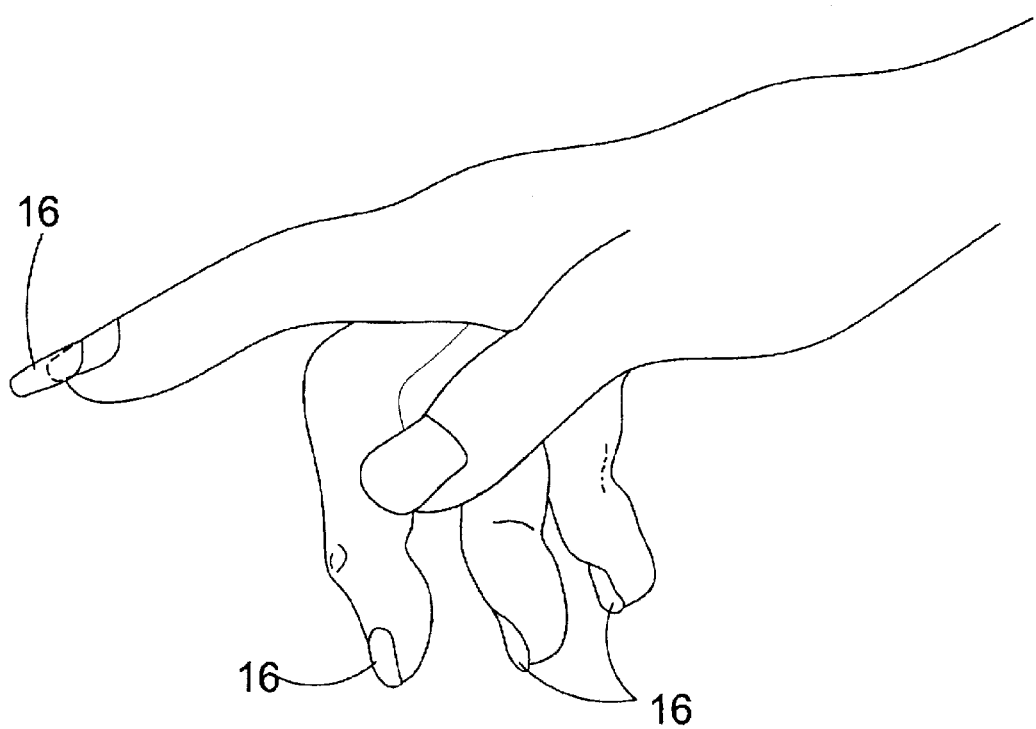
FIG. 4 is an illustrative view of the present invention preparation procedure steps.

Turning to FIG. 4, shown therein is an illustrative view of the preparation procedure steps of the present invention. First the nails 16 must be cleaned with polish remover. If extension tips are desired, the tips are applied after cleaning of the nails. To finalize the preparation of the nail 16, gently file the entire nail's plate.

Figure 5:
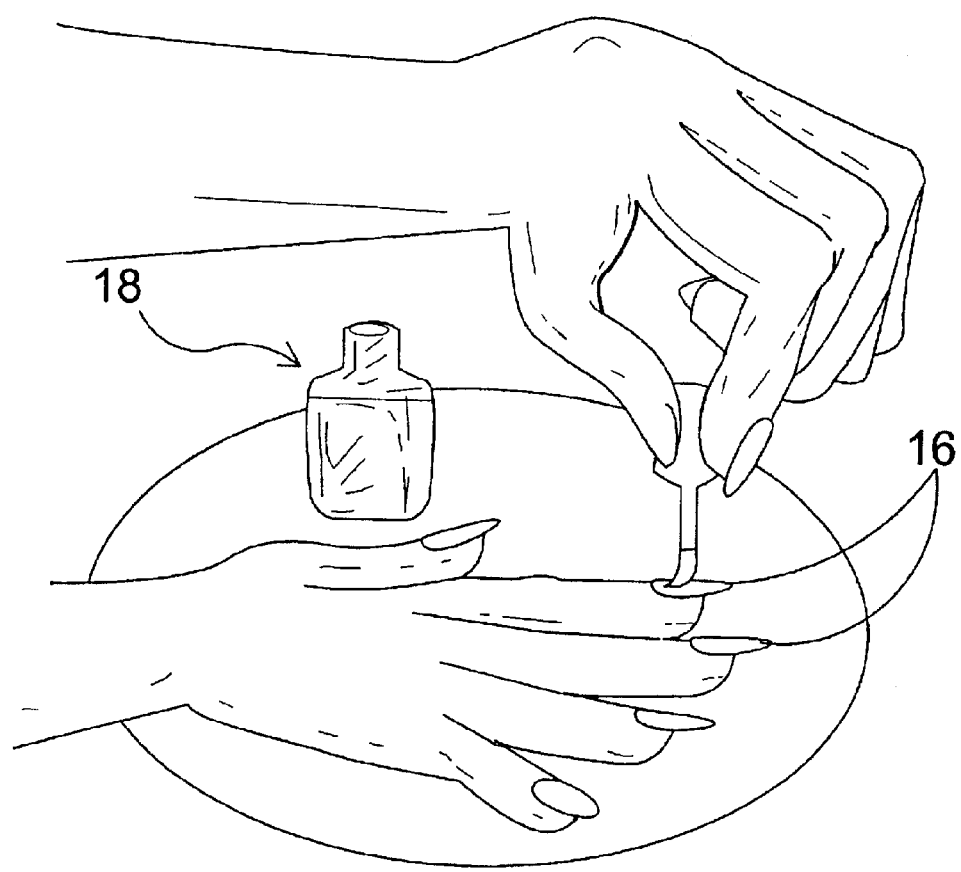
FIG. 5 is an illustrative view of the present invention initial coating procedure steps.

Turning to FIG. 5, shown therein is an illustrative view of the initial coating procedure steps of the present invention. Upon completion of the nail preparation, it will be necessary to put on one thin coat of gel blend or mix 18 on the entire nail's 16 plate using a pusher or other instrument that has a flat surface. The nails are then placed under a UV lamp for two minutes. After two minutes, a second coat of gel mix is applied to cover the first coat. It is then necessary to place the nails under the UV lamp for three minutes.

Figure 6:
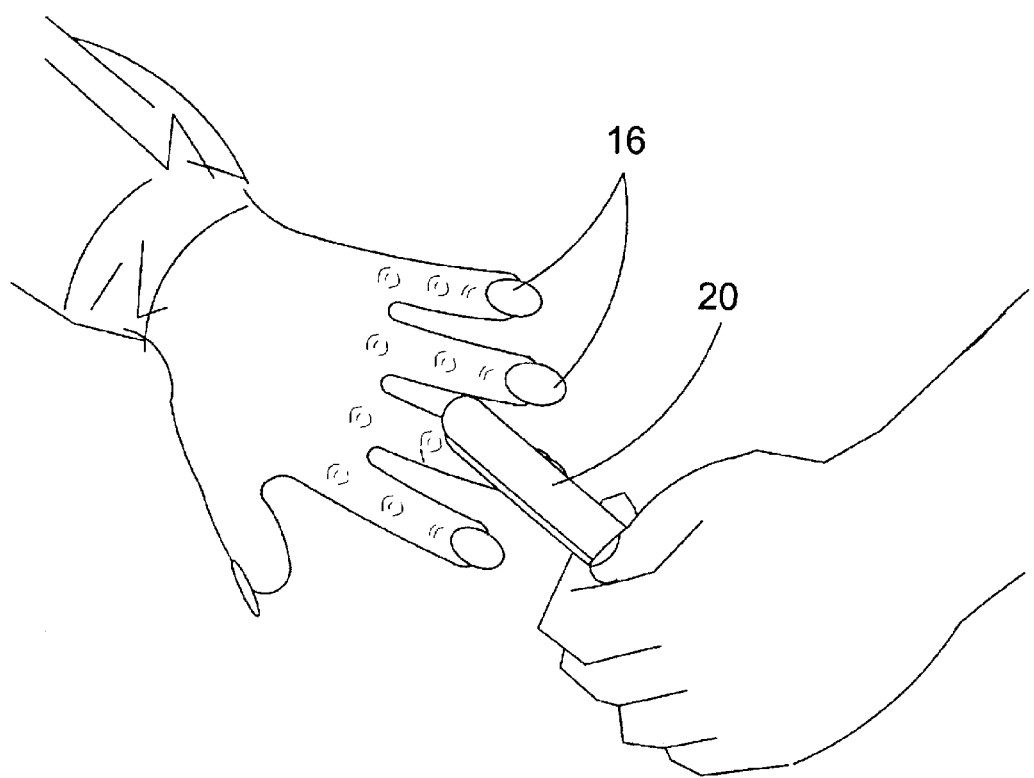
FIG. 6 is an illustrative view of the present invention shaping procedure steps.

Turning to FIG. 6, shown therein is an illustrative view of the shaping procedure steps of the present invention. After three minutes under the UV lamp as described in FIG. 5, the nails 16 are removed and wiped with alcohol. This is followed by filing with a nail file or drill 20 the entire nail to the desired thickness using the coarse side of the sand paper drill. Use the nail file 20 to shape the nail 16 as desired. This is followed by turning the nail 16 upside down to smooth all the edges underneath the nail. Upon completion, the file or drill's 20 medium side sand paper is used to smooth the entire nail 16. Also ensure the product is attached tightly around the cuticle, but no gel mix is applied on the cuticle. Finally, the excess powder is dusted away ensuring the nail 16 is clean.

Figure 7:
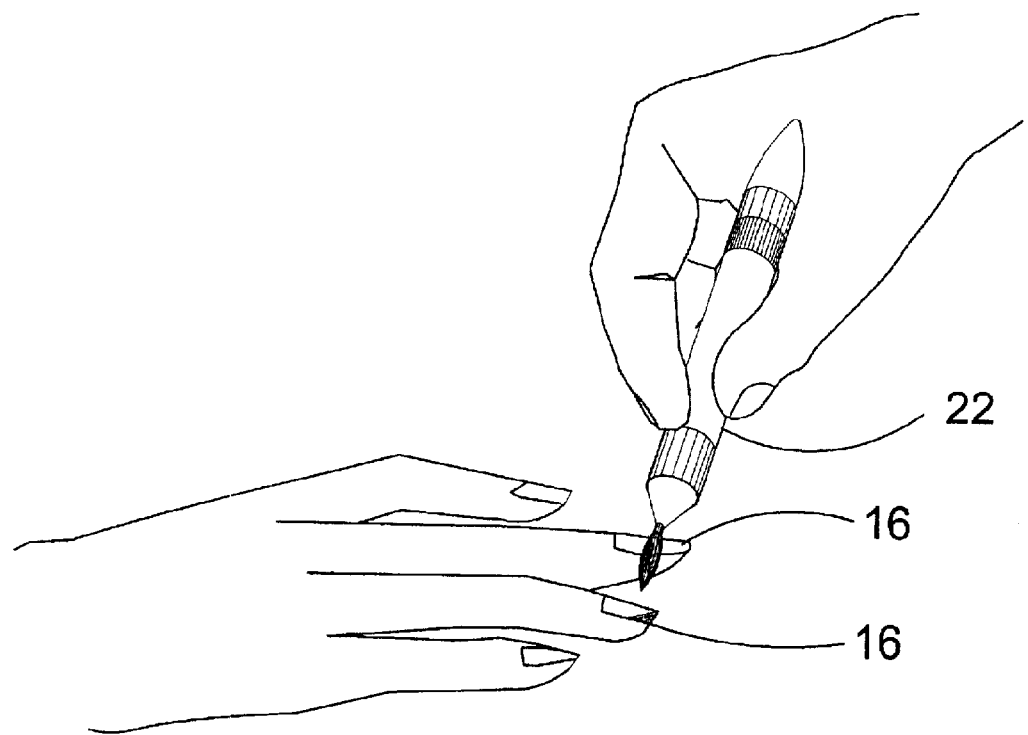
FIG. 7 is an illustrative view of the present invention optional French manicure.

Turning to FIG. 7, shown therein is an illustrative view of the optional French manicure of the present invention. If a French manicure is desired, it will be necessary to add white polish 22 to the nail 16 tip upon completion of the nail shaping procedure as described in FIG. 6, but before proceeding with final coating steps described in FIG. 8. The following gel blend and acrylic powder blend is combined for a natural look of pink and white French manicure. To prepare the pink portion, mix an equal amount of UV gel compound and pink acrylic powder. For the white portion, mix an equal amount of UV gel compound and white acrylic powder.

Figure 8:
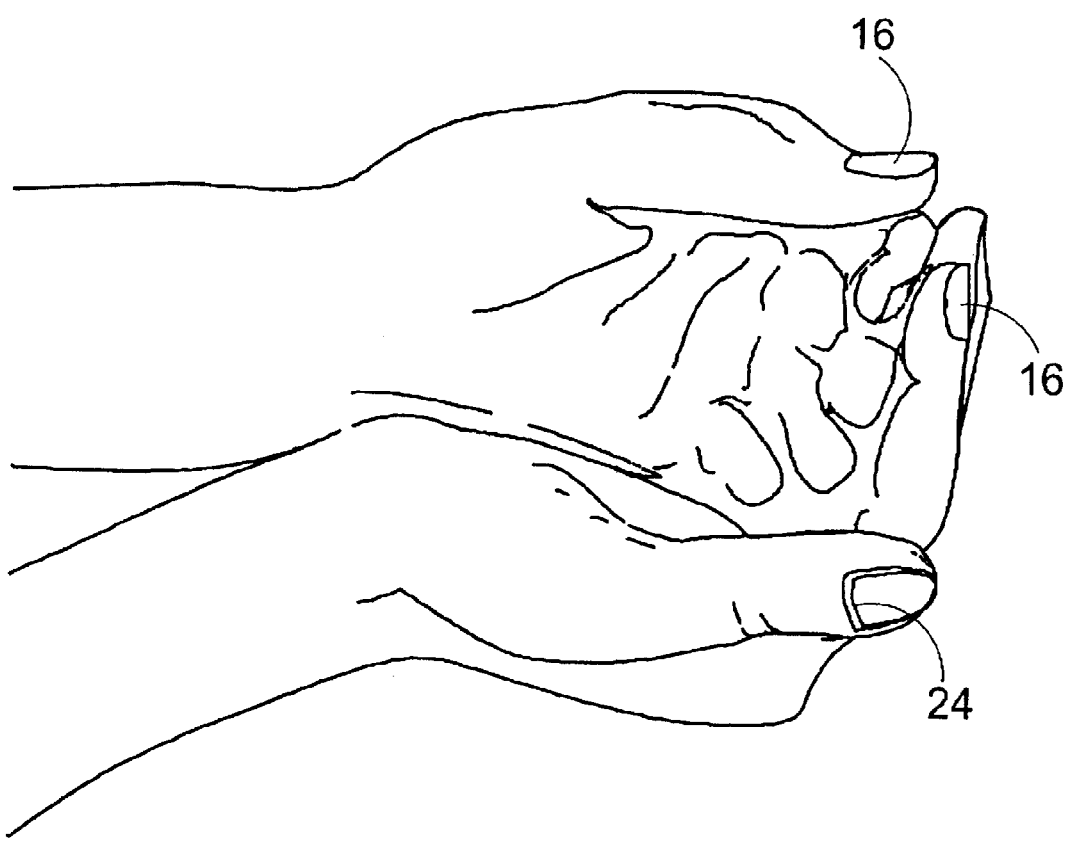
FIG. 8 is an illustrative view of the present invention procedure final steps.

Turning to FIG. 8, shown therein is an illustrative view of the final steps of the present invention. Upon completion of the nail shaping steps, it will be necessary to use a gel brush or the like to put on one thin coat of clear gel on the entire nail 16, applied one millimeter away from the cuticle 24, followed by UV lamp drying for two minutes. After two minutes, the gel brush is used to put on a second thin coat of clear gel on the entire nail 16, making sure to cover every coat on the nail carefully. This is followed by an additional five minutes under the UV lamp. After five minutes, the nail 16 is wiped with alcohol, cuticle oil is applied, and the process is completed with washing of the hands as shown.

Figure 9:
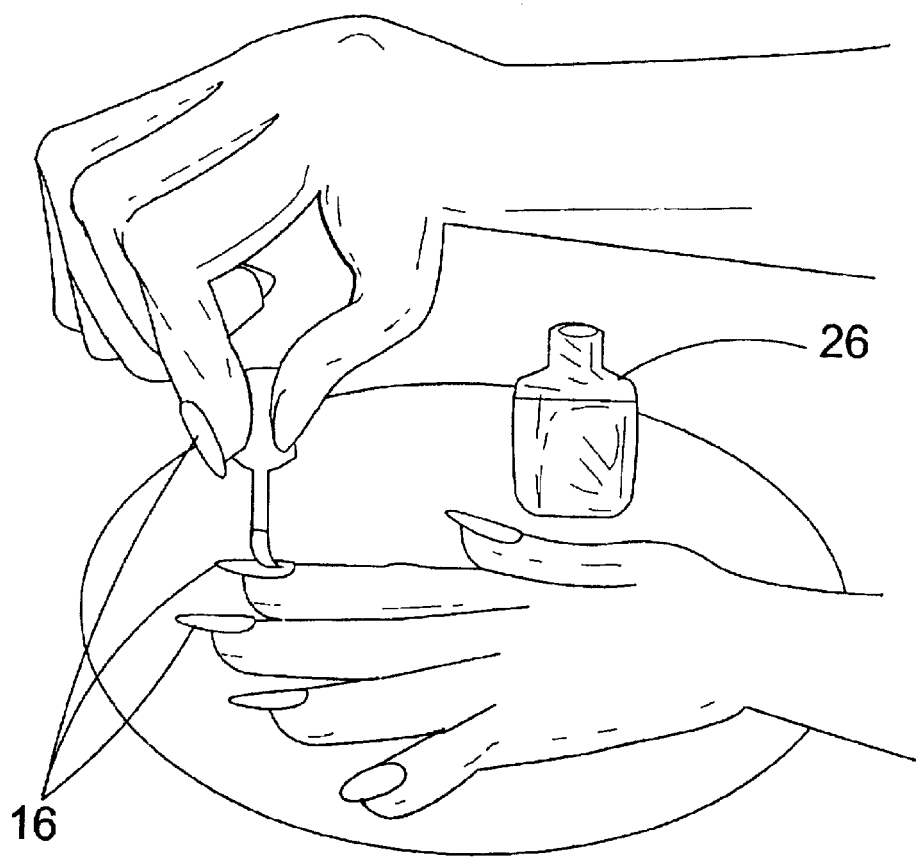
FIG. 9 is an illustrative view of the present invention procedure embodiment.

Turning to FIG. 9, shown therein is an illustrative view of the nail polishing steps of the present invention if this is desired. Upon completion of the final coating steps as described in FIG. 8, optional coats of color nail polish 26 can be applied to the nails 16 if desired.

Figure 10:
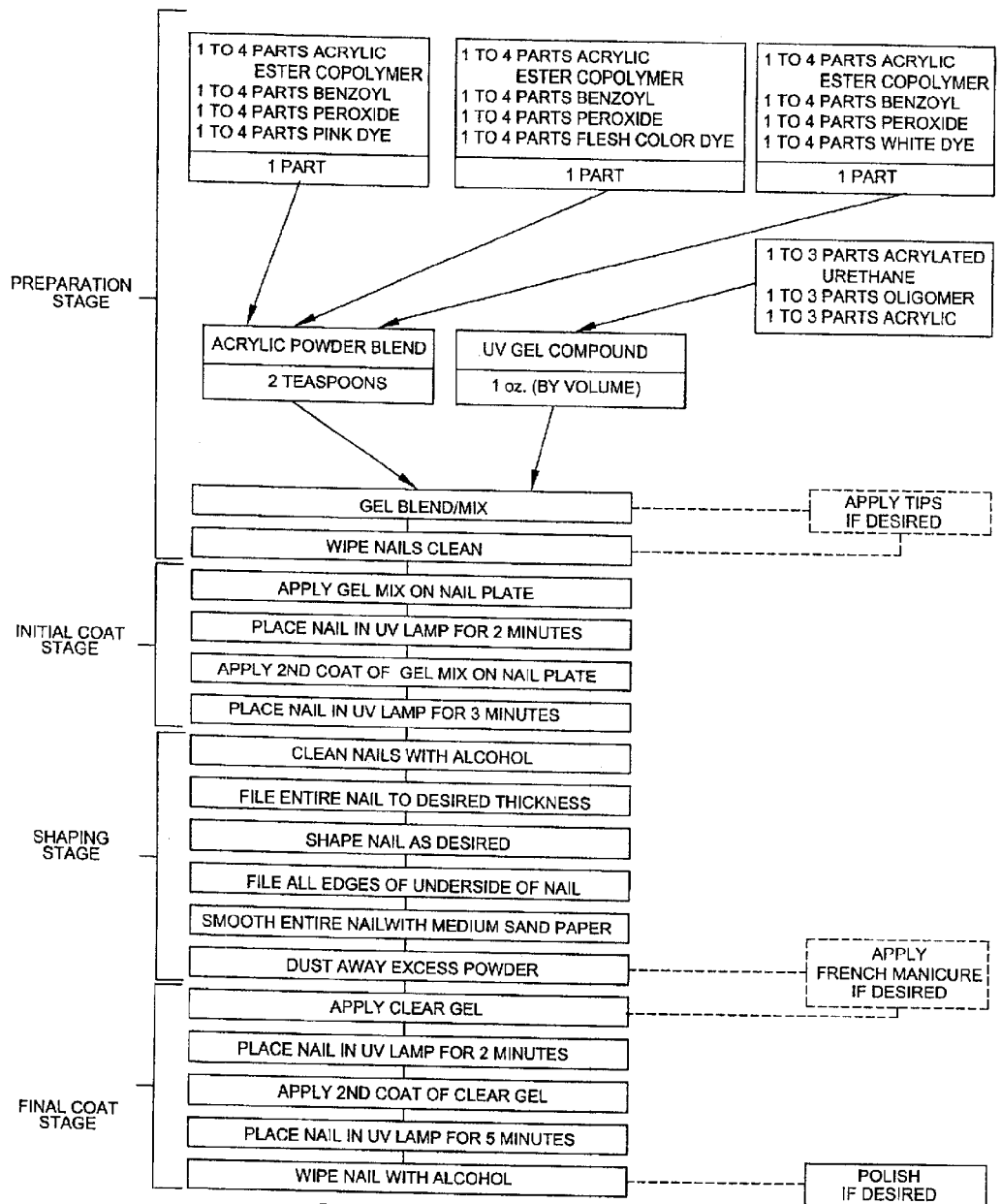
FIG. 10 is a flow chart of the present invention nail treatment process.

Turning to FIG. 10, shown therein is a flow chart of the entire nail treatment process of the present invention.

I claim:

1. A method of treating a natural fingernail of a user, comprising the steps of:
   a) preparing an acrylic powder blend by combining one part pink powder, one part flesh-colored powder and one part white powder;
   b) preparing a UV gel compound by mixing one to three parts acrylated urethane, one to three parts oligomer, and one to three parts acrylic;
   c) preparing a gel blend by mixing two teaspoons of the acrylic powder blend and one ounce by volume of UV gel compound;
   d) cleaning the fingernail of the user;
   e) applying the gel blend onto a plate of the fingernail;
   f) placing the fingernail under an ultraviolet lamp for about two minutes;
   g) applying a second coat of gel blend to the plate of the fingernail;
   h) placing the fingernail under an ultraviolet lamp for about three minutes;
   i) cleaning the fingernail with alcohol;
   j) filing the entire fingernail to the desired thickness;
   k) shaping the fingernail as desired with a file;
   l) filing all edges of the underside of the fingernail;
   m) smoothing the entire fingernail with medium sandpaper;
   n) dusting away the excess powder from the finger;
   o) applying a clear gel blend to the fingernail;
   p) placing the fingernail under an ultraviolet lamp for about two minutes;
   q) applying a second coat of clear gel;
   r) placing the gel under an ultraviolet lamp for about five minutes; and,
   s) wiping the fingernail with alcohol.

2. The method of claim 1, further comprising the steps of preparing the pink powder by mixing one to four parts ester acrylic copolymer, one to four parts benzoyl, one to four parts peroxide, and one to four parts pink dye.

3. The method of claim 2, further comprising the steps of preparing the flesh-colored powder by mixing one to four parts ester acrylic copolymer, one to four parts benzoyl, one to four parts peroxide, and one to four parts flesh-colored dye.

4. The method of claim 3, further comprising the steps of preparing the white powder by mixing one to four parts ester acrylic copolymer, one to four parts benzoyl, one to four parts peroxide, and one to four parts white dye.

5. The method of claim 4, wherein the gel blend is prepared by mixing two teaspoons of acrylic powder blend and one ounce by volume of UV gel compound.

6. The method of claim 1, further comprising the step of applying the tip to the fingernail between steps c) and d).

7. The method of claim 1, further comprising the step of applying a French manicure between steps n) and o).

8. The method of claim 1, further comprising the step of applying fingernail polish to the fingernail following step s).

* * * * *